United States Patent [19]

Liotta et al.

[11] Patent Number: 5,110,987
[45] Date of Patent: May 5, 1992

[54] METHOD OF PREPARING SPHINGOSINE DERIVATIVES

[75] Inventors: Dennis Liotta; Alfred H. Merrill, both of Stone Mountain, Ga.

[73] Assignee: Emory University, Atlanta, Ga.

[21] Appl. No.: 208,390

[22] Filed: Jun. 17, 1988

[51] Int. Cl.$^5$ .................................... C07C 209/54
[52] U.S. Cl. .................... 564/303; 564/304; 564/487
[58] Field of Search ............... 564/487, 303, 304

[56] References Cited

U.S. PATENT DOCUMENTS

| 2,194,294 | 3/1940 | Cass | 564/487 |
| 4,463,192 | 7/1984 | Duranleau | 564/487 |

FOREIGN PATENT DOCUMENTS 1444552  8/1976  United Kingdom .

OTHER PUBLICATIONS

CA) 109:110149g of Garner et al. J. Org. Chem 1988, 53(18) 4395-8.
CA) 109:230620a of Herold Helv. Chim. Acta 1988, 71(2) 354-62.
CA) 110:7935g of Radunz et al. Liebigs Ann. Chem 1988, (11), 1103-5.

*Primary Examiner*—Robert A. Wax
*Assistant Examiner*—Frederick F. Tsung
*Attorney, Agent, or Firm*—Needle & Rosenberg

[57] ABSTRACT

A method of preparing a substituted derivative of sphingosine comprising the steps of reducing serine methyl ester by a hydride reagent to form an aldehyde or aldehyde derivative, adding acetylide anions to the aldehyde to form an erythro-isomer or propargyl alcohol and inverting the propargyl alcohol by $S_N2$ inversion to form a threo-isomer. Either isomer can then be deprotected to form an alkyne with a 2-aminopropane 1,3-diol head group; this alkyne can be reduced to form sphingosine or a sphingosine derivitive which can be functionalized at the 4 and 5 positions to form a substituted derivative of sphingosine.

46 Claims, 3 Drawing Sheets

W = hydrogen, hydroxyl, alkoxy, amino, alkylamino, dialkylamino.

X = hydrogen, hydroxyl, alkoxy, amino, alkylamino, dialkylamino.

Y = hydrogen, hydroxyl, alkoxy, amino, alkylamino, dialkylamino.

Z = hydrogen, hydroxyl, alkoxy, amino, alkylamino, dialkylamino.

$R_1$ = hydrogen, alkyl, aryl.

$R_2$ = hydrogen, alkyl, aryl.

$R_3$ = hydrogen, alkyl, aryl.

METHOD OF PREPARING SPHINGOSINE DERIVATIVES

The U.S. Government has rights in this invention pursuant to Grant Nos. GM33369 and GM26908, Winship Cancer Center Grant from the National Institute of Health.

BACKGROUND OF THE INVENTION

The present invention relates to a method of preparing sphingosine derivatives, including, but not limited to, the four enantiomers of sphingosine.

Sphingolipids (i.e., ceramides, sphingomyelin and gangliosides) constitute a broad class of biologically important compounds. These materials are known to act as biological response modifiers, and have potential uses in the treatment of diseases in which the progression of the disease, or in which the therapy for the disease, involves growth factors, hormones, or a variety of drugs based on the mechanism of action of such compounds. For example, it is known that sphingosine is a potent inhibitor of protein kinase C in vivo and in vitro.

There exists a need, therefore, for a method of efficiently preparing sphingosine derivatives.

There also exists a need for a synthetic route to each of the sphingosine enantiomers which not only permits the stereoselective production and biological assay of these materials, but which also provides the flexibility to do extensive structure and function modifications.

SUMMARY OF THE INVENTION

The present invention relates to a method of preparing sphingosine derivatives. It also relates to the stereoselective synthesis of enantiomerically pure dihydroxyalkene primary amines and related compounds, including each of the four enantiomers of sphingosine from either L- or D- serine. Included in the method is the diastereoselective addition of acetylide anions to the following aldehyde to form propargyl alcohol with high erythro selectivity:

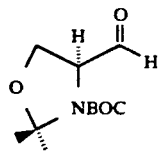

The erythro-isomer of propargyl alcohol is inverted by $S_N2$ inversion to form a threo-isomer. Either isomer can then be deprotected to form an alkyne with a 2-aminopropane 1,3-diol head group; this alkyne can be reduced to form sphingosine or a sphingosine derivative which can be functionalized at the 4 and 5 positions to form a substituted derivative of sphingosine. The aldehyde itself is prepared by reducing serine methyl ester by a hydride reagent, and particularly an aluminum hydride reagent such as is used in DIBAL reduction.

DETAILED DESCRIPTION OF THE INVENTION

The backbone component of sphingolipids is the long chain base sphingosine, which is typically present as its D(+)-erythro isomer (2S, 3R), that is:

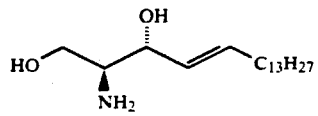

Figure 1:
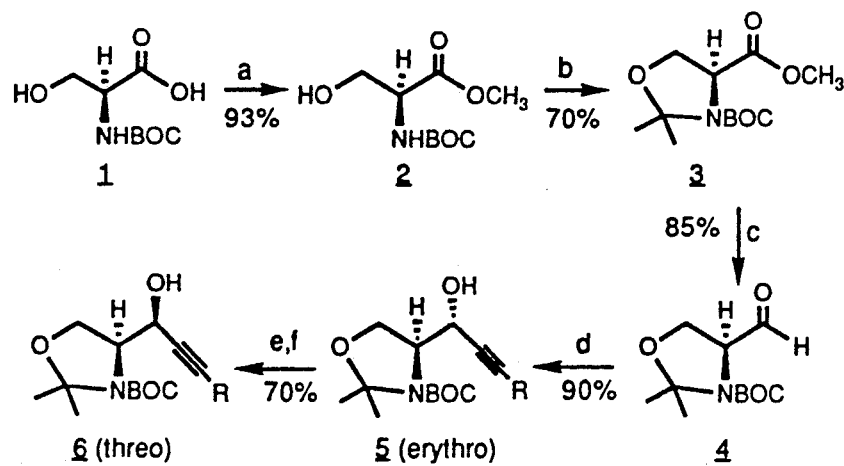
FIG. 1 illustrates the synthesis of sphingosine derivatives according to the present invention.
Figure 1:
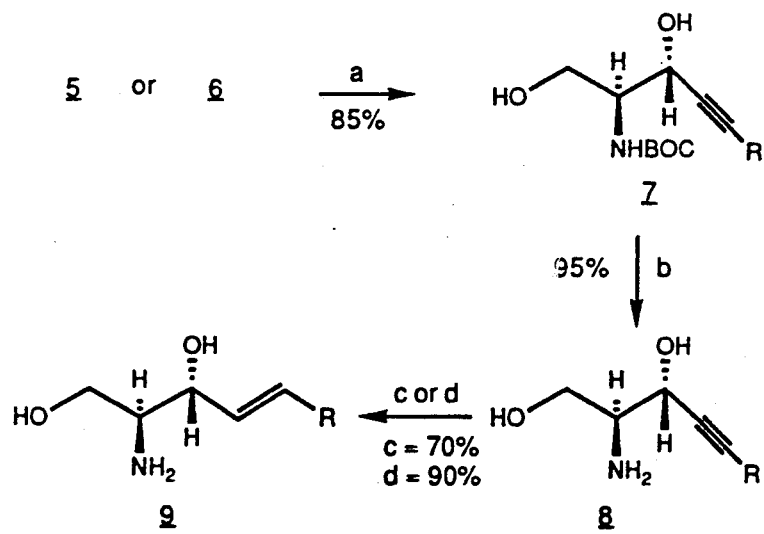

The process of the present invention is set forth in FIG. 1. Starting from either N-BOC-D- or L-serine (BOC=t-butyloxycarbonyl), one can produce a protected serine methyl ester 3 in approximately 62% overall yield by a series of standard synthetic manipulations, such as those set forth in FIG. 1. DIBAL reduction of the serine methyl ester 3 in toluene at −78° C. provides an approximately 85% yield of an aldehyde 4. The reduction may be carried out by using a hydride reagent which stops the reaction at the aldehyde oxidation state. For example, aluminum hydride reagents, including lithium aluminum hydride, have been found effective. The resulting aldehyde has a 2-aminopropane 1, 3 diol head group. This aldehyde 4 has been found to be an extremely useful intermediate for the preparation of sphingosine derivatives, and particularly each of the enantiomers of sphingosine.

It has been found that the addition of acetylide anions, and particularly alkali acetylides such as the lithium salt of pentadecyne in THF (−78° C. to 0° C.), to the aldehyde 4 produces propargyl alcohol 5 as an approximately 9:1 mixture of erythro- and threo-isomers, respectively, in approximately 90% isolated yield. The erythro- and threo-isomers may be readily separated by chromatography on silica gel (i.e. hexane/ethyl acetate, 2:1). Conversion of the propargyl alcohol 5 to dehydrosphingosine 8 may be achieved using any standard deprotection sequence, such as shown in FIG. 1.

To obtain erythro sphingosine 9 on a small scale (i.e. approximately 10–100 mg), dehydrosphingosine 8 was exposed to a refluxing solution of excess lithium in liquid ammonia/THF (1, 2, 3, 4-Tetrahydro-9-fluorenone) (4:1) for approximately 7 hours. This resulted in a quantitative recovery of a 9:1 mixture of the erythro sphingosine 9 and dehydrosphingosine 8, respectively. Pure erythro sphingosine 9 is obtained by recrystallization of the mixture from hexane.

To overcome problems associated with maintaining relatively constant amounts of ammonia during large scale dissolving metal reductions, the lithium aluminum hydride reduction is altered by switching solvents from refluxing THF (BP=67° C.) to refluxing DME (dimethoxyethane, BP=85° C.) for 12 hours. This results in consistent yields of 70% on scales up to 5 grams.

Figure 2:
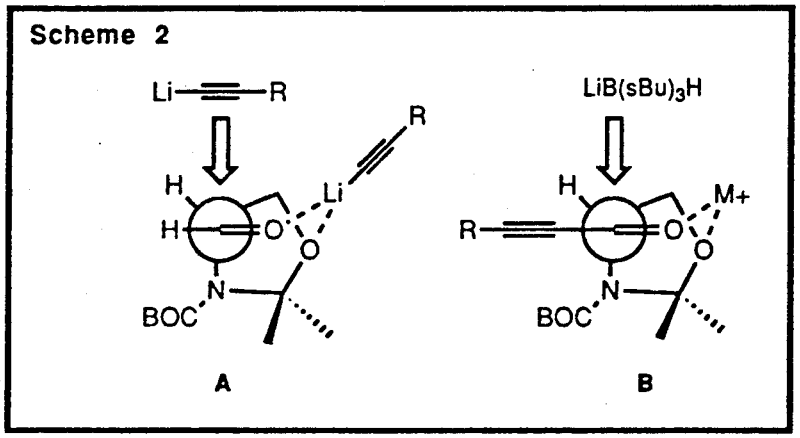
FIG. 2 illustrates a β-chelation controlled model according to the present invention.
Figure 2:
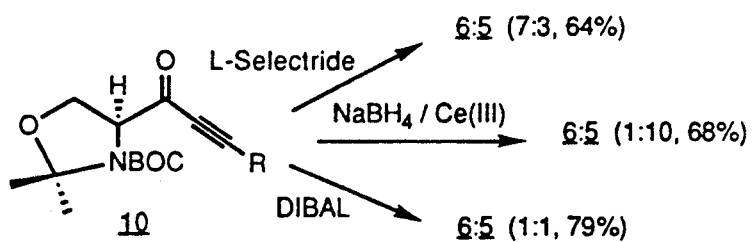

The erythro-selectivity in the conversion of the aldehyde 4 to propargyl alcohol 5 is shown in the β-chelation-controlled model set forth in FIG. 2. This β-chelation may be used as a means of inverting the stereochemistry of the C-3 alcohol to obtain the corresponding threo-isomer by converting propargyl alcohol to its corresponding ketone 10, shown in FIG. 3, by Swern oxidation to provide an 80% yield, followed by subsequent reduction. Erythro alcohol 5 has been found to be cleanly isomerized to its corresponding threo-isomer 6 in 70% yield by Mitsunobu inversion of the C-3 alcohol. The threo-isomer 6 can then be converted to threo-sphingosine in yields which are consistently within 2% of those obtained in the erythro series.

Illustrative examples of the synthesis of sphingosine derivatives according to the present invention are as follows:

EXAMPLE 1

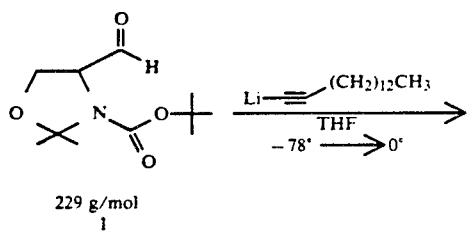

229 g/mol
1

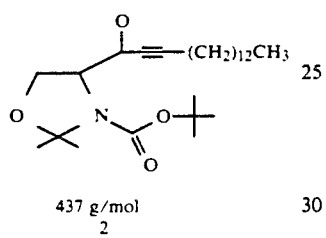

437 g/mol
2

(1.3 eq, 56.7 mmol, 11.8 gms, 14.9 mls) 1-pentadecyne was dissolved in 400 mls by THF and cooled to −78° C. and stirred under $N_2$ atmosphere. (1.3 eq, 3.6 gms) n-BuLi was then added in 1 ml increments and after the last addition, reaction mixture was stirred for 30 min. (10 gms, 1 eq) of the aldehyde was dissolved in 60 mls THF and added dropwise over a 1 hr period. After the aldehyde was added, the reaction mixture was stirred for an additional 30 mins at −78° C., then brought to 0° for 2 hrs. The reaction was quenched with saturated $NH_4Cl$ at 0°, brought to room temperature, THF was evaporated, diluted with $Et_2O$, and the aqueous layer was separated and discarded. The organic layer was washed with water, brine and dried over $MgSO_4$, and the ether was evaporated in vacuo.

| Percent yield: 86% | Purification: Flash column |
|---|---|
| RF = 0.5 | 1:7 EtOAc/Hexanes |
| (EtOAc/Hexanes 1:2) | Erythro/Threo: 9:1 |

EXAMPLE 2

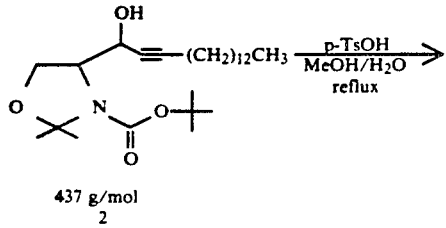

437 g/mol
2

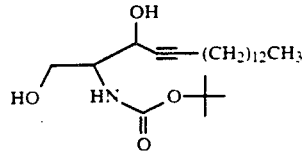

(5 gms, 11.4 mmol) of alkynol 2 was dissolved in 250 mls MeOH and 100 mls water and the reaction mixture was stirred (upon addition of water, the reaction mixture becomes milky white). 400 mgs TsOH is added and the reaction is refluxed for 4 hrs. Evaporate in vacuo MeOH. 400 mls EtOAc was added and mixture was basified with saturated $NaHCO_3$, the layers were separated and organic layer washing with water and brine, and dried over $MgSO_4$. EtOAc was evaporated in vacuo.

| Percent Yield: 86% | Product recrystallized |
|---|---|
| RF = 0.18 | from $Et_2O$/Hexane |
| (EtOA c/Hexane 1:2) | |

EXAMPLE 3

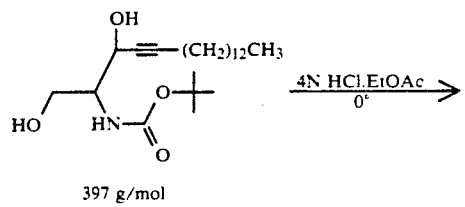

397 g/mol
3

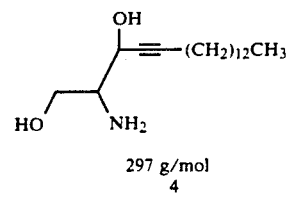

297 g/mol
4

(5 gms, 12.6 mmol) of alkynol 3 was dissolved in 100 mls EtOAc and cooled to 0° C. 100 mls of 4N EtOAc was added at 0° C. and the reaction stirred for 4 hrs. The reaction was quenched with 10% $NH_4OH$ and basified to pH > 10. The aqueous layer was separated and extracted 3 times with 50 mls EtOAc. The organic layers were combined and washed with water and brine, dried over $MgSO_4$ and EtOAc was evaporated in vacuo.

| Percent yield: 90% | Purification recrystallized |
|---|---|
| | from $Et_2O$/hexanes |

EXAMPLE IV

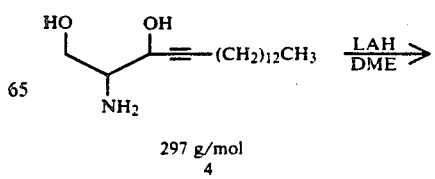

297 g/mol
4

-continued

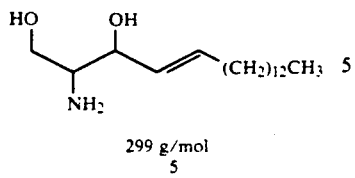

299 g/mol
5

(1 gm, 3.37 mmol) of alkynol 4 was dissolved in 30 mls DME (1,2-dimethoxyethane). 1.5 gms LAH was added as the reaction was refluxed under N₂ atmosphere for 24 hrs. The reaction was quenched with dilute NaOH and then diluted with Et₂O and hexanes. The salts were stirred for 30 min and the mixture was filtered. The filtrate was washed with Et₂O. The organics were dried over MgSO₄ and the solvents were evaporated in vacuo.

| Percent yield: 95% | Purification: recrystallization in CHCl₃/hexanes |
|---|---|

EXAMPLE V

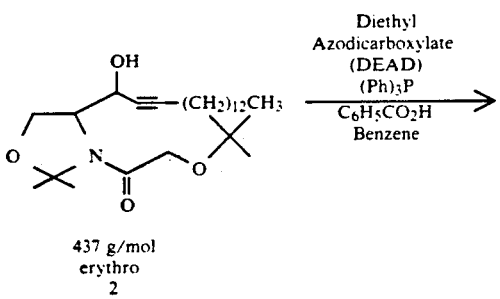

437 g/mol
erythro
2

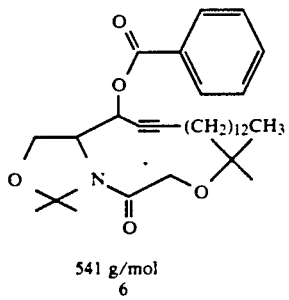

541 g/mol
6

Alkynol 2 (3 gms, 6.87 mmol) and (Ph)₃P(1.1 eq, 7.55 mmol, 1.98 gms) were dissolved in 40 mls dry benzene and stirred for 30 mins under N₂ atmosphere. Benzoic acid (1.1 eq, 7.55 mol, 0.92 gms) in 20 mls benzene was then added followed by DEAD (1.2 eq, 8.23 mmol, 1.43 gms, 1.30 mls) also in 20 mls of benzene. The reaction was stirred for 24 hours, the benzene was evaporated in vacuo, diluted with Et₂O, and the organic layer was extracted with NaHCO₃, water, and brine. The organics were dried with MgSO₄ and evaporated in vacuo.

| Percent yield: 69% RF = 0.78 (EtOAc:hexanes 1:2) | Purification: Flash column EtOAc:Hexanes (1:10) |
|---|---|

EXAMPLE VI

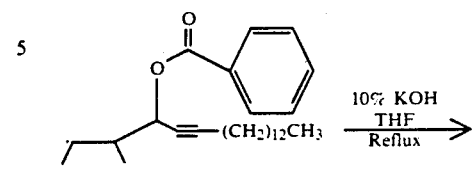

541 g/mol
6

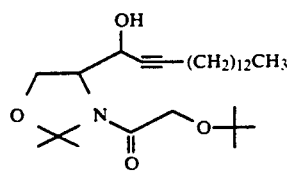

432 g/mol
threo
7

(1 gm, 1.85 mmol) of compound 6 was dissolved in 50 mls THF and 50 mls of 10% KOH was then added. The reaction was refluxed for 24 hrs, the THF evaporated in vacuo, diluted with Et₂O, and the layers were separated. The organic layer was extracted with H₂O and brine, dried over MgSO₄ and evaporated in vacuo.

| Percent yield: 90% RF = 0.5 | Purification: Flash column ETOAc:Hexanes (1:5) |
|---|---|

Figure 3:
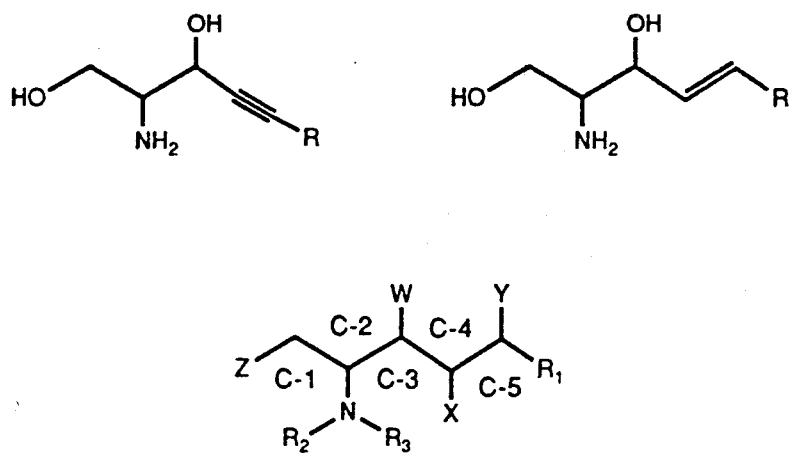
FIG. 3 illustrates a potential compound capable of being prepared according to the present invention.

The present invention provides a synthesis which allows the preparation of sphingosine derivatives, and particularly each of the four enantiomers of sphingosine on a multigram scale. Furthermore, the sequence permits easy modification of head group functionality, i.e., substitution at nitrogen or oxygen, and hydrophobicity by the addition of alkyne of different chain lengths to the aldehyde 4. This is shown in FIG. 3, wherein the modification may include the substitution of either hydrogen, hydroxyl, alkoxy, amino, alkylamino or dialkylamino at sites W, X, Y and/or Z. Also, hydrogen, alkyl or aryl may be added to sites $R_1$, $R_2$ and/or $R_3$. The process particularly allows the synthesis in an enantiomerically pure state of all possible configurations at C-2, C-3, C-4 and C-5.

What is claimed is:

1. A method of preparing a threo-isomer of a derivative of sphingosine, wherein said derivative of sphingosine comprises the formula:

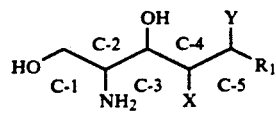

wherein X and Y are selected from the group consisting essentially of hydrogen, hydroxyl, alkoxy, amino, alkylamino and dialkylamino and wherein $R_1$ is selected from the group consisting essentially of hydrogen, alkyl and aryl, comprising the steps of:

a) adding acetylide anions to an aldehyde or a derivative of said aldehyde that is capable of forming said derivative of sphingosine in substantially the same manner as said aldehyde to form an erythro-isomer of propargyl alcohol, said aldehyde having the formula:

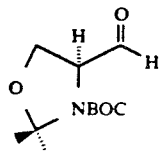

b) inverting said propargyl alcohol by $S_N2$ inversion to form a threo-isomer of propargyl alcohol;
c) acidifying said threo-isomer to form a diol having the formula:

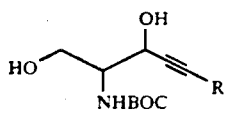

wherein R is selected from the group consisting essentially of hydrogen, alkyl and aryl;
d) cleaving said diol to form an amine having the formula:

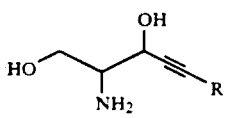

e) reducing said amine to form an alkene having the formula:

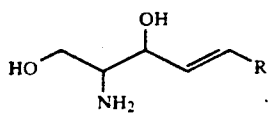

and
f) adding a functional group selected from the group consisting of hydrogen, hydroxyl, alkoxy, amino, alkylamino, and dialkylamino to the 4 and 5 position of said alkene to form said threo-isomer of a derivative of sphingosine.

2. The method of claim 1, wherein said acetylide anions comprise alkali acetylides.

3. The method of claim 1, wherein said acetylide anions comprise 1-lithiopentadecyne.

4. The method of claim 1, wherein said $S_N2$ inversion is a Mitsunobu inversion.

5. The method of claim 1, wherein said substituted derivative of sphingosine has a 2-aminopropane 1,3 diol head group.

6. The method of claim 1, further comprising the step of adding a functional group to said derivative of sphingosine to form a compound of the formula:

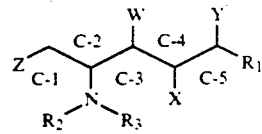

wherein W is selected from the group consisting essentially of hydrogen, hydroxyl, alkoxy, amino, alkylamino and dialkyamino;
wherein X is selected from the group consisting essentially of hydrogen, hydroxyl, alkoxy, amino, alkylamino and dialkyamino;
wherein Y is selected from the group consisting essentially of hydrogen, hydroxyl, alkoxy, amino, alkylamino and dialkyamino;
wherein Z is selected from the group consisting essentially of hydrogen, hydroxyl, alkoxy, amino, alkylamino and dialkyamino;
wherein $R_1$ is selected from the group consisting essentially of hydrogen, alkyl and aryl;
wherein $R_2$ is selected from the group consisting essentially of hydrogen, alkyl and aryl;
wherein $R_3$ is selected from the group consisting essentially of hydrogen, alkyl and aryl.

7. A method of preparing a threo-isomer of a derivative of sphingosine, wherein said derivative of sphingosine comprises the formula:

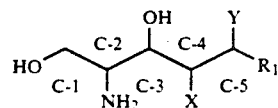

wherein X and Y are selected from the group consisting essentially of hydrogen, hydroxyl, alkoxy, amino, alkylamino and dialkylamino and wherein $R_1$ is selected from the group consisting essentially of hydrogen, alkyl and aryl, comprising:

a) reducing serine methyl ester by a hydride reagent to from an aldehyde or aldehyde derivative that is capable of forming said derivative of sphingosine in substantially the same manner as said aldehyde, said aldehyde having the formula:

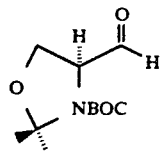

b) adding acetylide anions to said aldehyde or aldehyde derivative to form an erythro-isomer of propargyl alcohol;
c) inverting said propargyl alcohol by $S_N2$ inversion to form a threo-isomer of propargyl alcohol;
d) acidifying said threo-isomer to form a diol having the formula:

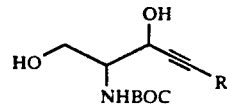

wherein R is selected from the group consisting essentially of hydrogen, alkyl and aryl;

e) cleaving said diol to form an amine having the formula:

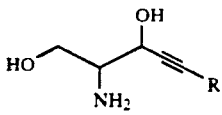

f) reducing said amine to form an alkene having the formula:

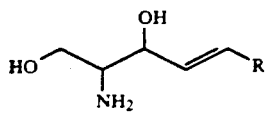

and g) adding a functional group selected from the group consisting of hydrogen, hydroxyl, alkoxy, amino, alkylamino, and dialkylamino to the 4 and 5 position of said alkene to form said threo-isomer of a derivative of sphingosine.

8. The method of claim 7, wherein said hydride reagent is an aluminum hydride reagent.

9. The method of claim 7, wherein said hydride reagent is lithium aluminum hydride.

10. The method of claim 7, wherein said reduction of serine methyl ester is accomplished by DIBAL reduction.

11. The method of claim 7, wherein said acetylide anions comprise alkali acetylides.

12. The method of claim 7, wherein said acetylide anions comprise 1-lithiopentadecyne.

13. The method of claim 7, wherein said $S_N2$ inversion is a Mitsunobu inversion.

14. The method of claim 7, wherein said substituted derivative of sphingosine has a 2-aminopropane 1,3 diol head group.

15. The method of claim 7, further comprising the step of adding a functional group to said derivative of sphingosine to form a compound of the formula:

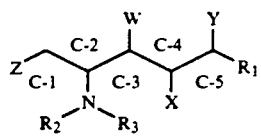

wherein W is selected from the group consisting essentially of hydrogen, hydroxyl, alkoxy, amino, alkylamino and dialkyamino;

wherein X is selected from the group consisting essentially of hydrogen, hydroxyl, alkoxy, amino, alkylamino and dialkyamino;

wherein Y is selected from the group consisting essentially of hydrogen, hydroxyl, alkoxy, amino, alkylamino and dialkyamino;

wherein Z is selected from the group consisting essentially of hydrogen, hydroxyl, alkoxy, amino, alkylamino and dialkyamino;

wherein $R_1$ is selected from the group consisting essentially of hydrogen, alkyl and aryl;

wherein $R_2$ is selected from the group consisting essentially of hydrogen, alkyl and aryl;

wherein $R_3$ is selected from the group consisting essentially of hydrogen, alkyl and aryl.

16. The method of claim 1, wherein said derivative of sphingosine comprises the formula:

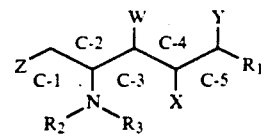

wherein W is hydroxyl;
wherein X is hydrogen;
wherein Y is hydroxyl;
wherein Z is hydroxyl;
wherein $R_1$ is alkyl;
wherein $R_2$ is hydrogen, and
wherein $R_3$ is hydrogen.

17. A method of preparing an erythro isomer of a derivative of sphingosine, wherein said derivative of sphingosine comprises the formula:

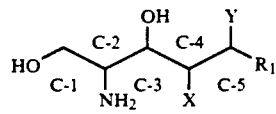

wherein X and Y are selected from the group consisting essentially of hydrogen, hydroxyl, alkoxy, amino, alkylamino and dialkylamino and wherein $R_1$ is selected from the group consisting essentially of hydrogen, alkyl and aryl, comprising the steps of:

a) adding acetylide anions to an aldehyde or a derivative of said aldehyde that is capable of forming said derivative of sphingosine in substantially the same manner as said aldehyde to form an erythro-isomer of propargyl alcohol, said aldehyde having the formula:

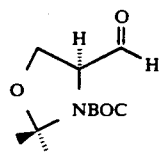

b) acidifying said propargyl alcohol to form a diol having the formula:

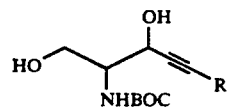

wherein R is selected from the group consisting essentially of hydrogen, alkyl and aryl;

c) cleaving said diol to form an amine having the formula:

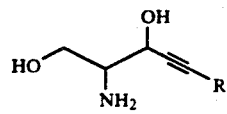

d) reducing said amine to form an alkene having the formula:

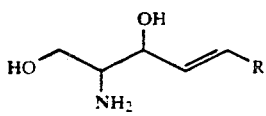

and e) adding a functional group selected from the group consisting of hydrogen, hydroxyl, alkoxy, amino, alkylamino, and dialkylamino to the 4 and 5 position of said alkene to form said erythro-isomer of a derivative of sphingosine.

18. The method of claim 17, wherein said acetylide anions comprise alkali acetylides.

19. The method of claim 17, wherein said acetylide anions comprise 1-lighiopentadecyne.

20. The method of claim 17, wherein said substituted derivative of sphingosine has a 2-aminopropane 1,3-diol head group.

21. The method of claim 17, further comprising the step of adding a functional group to said derivative of sphingosine to form a compound of the formula:

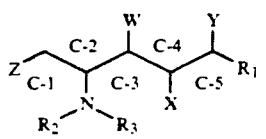

wherein W is selected from the group consisting essentially of hydrogen, hydroxyl, alkoxy, amino, alkylamino and dialkyamino;

wherein X is selected from the group consisting essentially of hydrogen, hydroxyl, alkoxy, amino, alkylamino and dialkyamino;

wherein Y is selected from the group consisting essentially of hydrogen, hydroxyl, alkoxy, amino, alkylamino and dialkyamino;

wherein Z is selected from the group consisting essentially of hydrogen, hydroxyl, alkoxy, amino, alkylamino and dialkyamino;

wherein $R_1$ is selected from the group consisting essentially of hydrogen, alkyl and aryl;

wherein $R_2$ is selected from the group consisting essentially of hydrogen, alkyl and aryl;

wherein $R_3$ is selected from the group consisting essentially of hydrogen, alkyl and aryl.

22. A method of preparing an erythro isomer of a derivative of sphingosine, wherein said derivative of sphingosine comprises the formula:

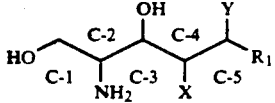

wherein X and Y are selected from the group consisting essentially of hydrogen, hydroxyl, alkoxy, amino, alkylamino and dialkylamino and wherein $R_1$ is selected from the group consisting essentially of hydrogen, alkyl and aryl, comprising:

a) reducing serine methyl ester by a hydride reagent to form an aldehyde or aldehyde derivitive that is capable of forming said derivative of sphingosine in substantially the same manner as said aldehyde, said aldehyde having the formula:

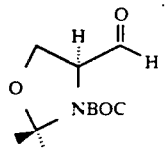

b) adding acetylide anions to an aldehyde or aldehyde derivative to form an erythro-isomer of propargyl alcohol;

c) acidifying said erythro-isomer to form a diol having the formula:

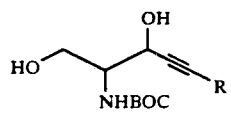

wherein R is selected from the group consisting essentially of hydrogen, alkyl and aryl;

d) cleaving said diol to form an amine having the formula:

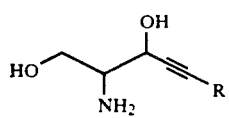

e) reducing said amine to form an alkene having the formula:

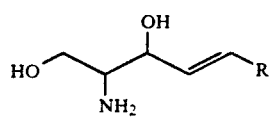

and f) adding a functional group selected from the group consisting of hydrogen, hydroxyl, alkoxy, amino, alkylamino, and dialkylamino to the 4 and 5 position of said alkene to form said erythro-isomer of a derivative of sphingosine.

23. The method of claim 22, wherein said hydride reagent is an aluminum hydride reagent.

24. The method of claim 22, wherein said hydride reagent is lithium aluminum hydride.

25. The method of claim 22, wherein said reduction of serine methyl ester is accomplished by DIBAL reduction.

26. The method of claim 22, wherein said acetylide anions comprise alkali acetylides.

27. The method of claim 22, wherein said acetylide anions comprise 1-lithiopentadecyne.

28. The method of claim 22, wherein said substituted derivative of sphingosine has a 2-aminopropane-1,3-diol head group.

29. The method of claim 22, further comprising the step of adding a functional group to said derivative of sphingosine to form a compound of the formula:

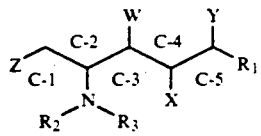

wherein W is selected from the group consisting essentially of hydrogen, hydroxyl, alkoxy, amino, alkylamino and dialkyamino;

wherein X is selected from the group consisting essentially of hydrogen, hydroxyl, alkoxy, amino, alkylamino and dialkyamino;

wherein Y is selected from the group consisting essentially of hydrogen, hydroxyl, alkoxy, amino, alkylamino and dialkamino;

wherein Z is selected from the group consisting essentially of hydrogen, hydroxyl, alkoxy, amino, alkylamino and dialkyamino;

wherein $R_1$ is selected from the group consisting essentially of hydrogen, alkyl and aryl;

wherein $R_2$ is selected from the group consisting essentially of hydrogen, alkyl and aryl;

wherein $R_3$ is selected from the group consisting essentially of hydrogen, alkyl and aryl.

30. A method of preparing a threo-isomer of sphingosine or a derivative thereof, wherein said derivative of sphingosine comprises the formula:

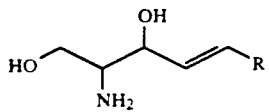

wherein $R_1$ is selected from the group consisting essentially of hydrogen, alkyl and aryl, comprising the steps of:

a) adding acetylide anions to an aldehyde or a derivative of said aldehyde that is capable of forming said sphingosine or derivative thereof in substantially the same manner as said aldehyde to form an erythro-isomer of propargyl alcohol, said aldehyde having the formula:

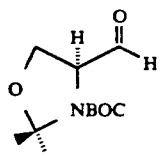

b) inverting said propargyl alcohol by $S_N2$ inversion to form a threo-isomer of propargyl alcohol;

c) acidifying said threo-isomer to form a diol having the formula:

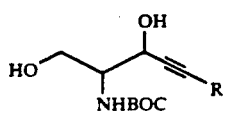

wherein R is selected from the group consisting essentially of hydrogen, alkyl and aryl;

d) cleaving said diol to form an amine having the formula:

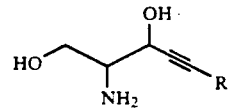

and e) reducing said amine to form an alkene having the formula:

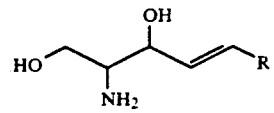

31. The method of claim 30, wherein said acetylide anions comprise alkali acetylides.

32. The method of claim 30, wherein said acetylide anions comprise 1-lithiopentadecyne.

33. The method of claim 30, wherein said $S_N2$ inversion is a Mitsunobu inversion.

34. The method of claim 30, wherein said derivative of sphingosine has a 2-aminopropane 1,3-diol head group.

35. The method of claim 30, further comprising the step of adding a functional group to said derivative of sphingosine to form a compound of the formula:

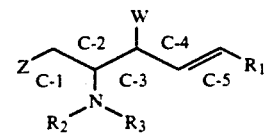

wherein W is selected from the group consisting essentially of hydrogen, hydroxyl, alkoxy, amino, alkylamino and dialkyamino;

wherein Z is selected from the group consisting essentially of hydrogen, hydroxyl, alkoxy, amino, alkylamino and dialkyamino;

wherein $R_1$ is selected from the group consisting essentially of hydrogen, alkyl and aryl;

wherein $R_3$ is selected from the group consisting essentially of hydrogen, alkyl and aryl;

wherein $R_3$ is selected from the group consisting essentially of hydrogen, alkyl and aryl.

36. A method of preparing an erythro-isomer of sphingosine or a derivative thereof, wherein said derivative of sphingosine comprises the formula:

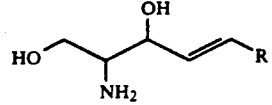

wherein $R_1$ is selected from the group consisting essentially of hydrogen, alkyl and aryl, comprising the steps of:

a) adding acetylide anions to an aldehyde or a derivative of said aldehyde that is capable of forming said sphingosine or derivative thereof in substantially the same manner as said aldehyde to form an erythro-isomer of propargyl alcohol, said aldehyde having the formula:

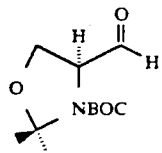

b) acidifying said propargyl alcohol to form a diol having the formula:

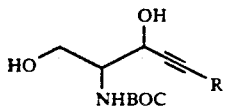

wherein R is selected from the group consisting essentially of hydrogen, alkyl and aryl;

c) cleaving said diol to form an amine having the formula:

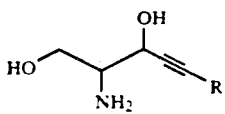

and d) reducing said amine to form an alkene having the formula:

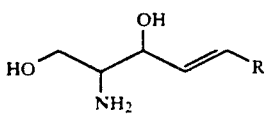

37. The method of claim 36, wherein said acetylide anions comprise alkali acetylides.

38. The method of claim 36, wherein said acetylide anions comprise 1-lithiopentadecyne.

39. The method of claim 36, wherein said derivative of sphingosine has a 2-aminopropane 1,3-diol head group.

40. The method of claim 36, further comprising the step of adding a functional group to said derivative of sphingosine to form a compound of the formula:

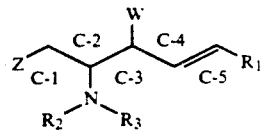

wherein W is selected from the group consisting essentially of hydrogen, hydroxyl, alkoxy, amino, alkylamino and dialkyamino;

wherein Z is selected from the group consisting essentially of hydrogen, hydroxyl, alkoxy, amino, alkylamino and dialkyamino;

wherein $R_1$ is selected from the group consisting essentially of hydrogen, alkyl and aryl;

wherein $R_2$ is selected from the group consisting essentially of hydrogen, alkyl and aryl;

wherein $R_3$ is selected from the group consisting essentially of hydrogen, alkyl and aryl.

41. The method of claim 1, wherein approximately equal molar ratios of said acetylide anions and said aldehyde react.

42. The method of claim 7, wherein approximately equal molar ratios of said acetylide anions and said aldehyde react.

43. The method of claim 17, wherein approximately equal molar ratios of said acetylide anions and said aldehyde react.

44. The method of claim 22, wherein approximately equal molar ratios of said acetylide anions and said aldehyde react.

45. The method of claim 30, wherein approximately equal molar ratios of said acetylide anions and said aldehyde react.

46. The method of claim 36, wherein approximately equal molar ratios of said acetylide anions and said aldehyde react.

* * * * *

UNITED STATES PATENT AND TRADEMARK OFFICE
CERTIFICATE OF CORRECTION

Page 1 of 2

PATENT NO. : 5,110,987
DATED : May 5, 1992
INVENTOR(S) : Dennis C. Liotta

It is certified that error appears in the above-indentified patent and that said Letters Patent is hereby corrected as shown below:

Column 3, lines 20-32, the corrected figure should appear after the reaction arrow as:

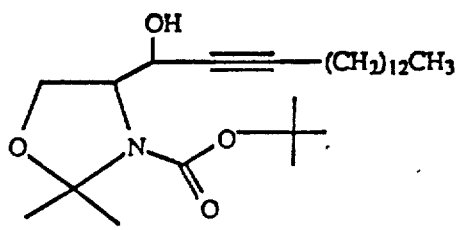

437 g/mol
2

UNITED STATES PATENT AND TRADEMARK OFFICE
CERTIFICATE OF CORRECTION

PATENT NO. : 5,110,987
DATED : May 5, 1992
INVENTOR(S) : Dennis C. Liotta

It is certified that error appears in the above-indentified patent and that said Letters Patent is hereby corrected as shown below:

Claim 35, Column 14, line 46, delete "$R_3$ and substitute -- $R_2$ --.

Signed and Sealed this

Twenty-first Day of December, 1993

Attest:

BRUCE LEHMAN

*Attesting Officer*     *Commissioner of Patents and Trademarks*